(12) United States Patent
Hossainy et al.

(10) Patent No.: US 7,169,173 B2
(45) Date of Patent: *Jan. 30, 2007

(54) COMPOSITE STENT WITH REGIOSELECTIVE MATERIAL AND A METHOD OF FORMING THE SAME

(75) Inventors: Syed F. A. Hossainy, Fremont, CA (US); Orlando Padilla, Laguna Beach, CA (US); Daryush Mirzaee, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/668,781

(22) Filed: Sep. 22, 2003

(65) Prior Publication Data

US 2004/0098117 A1 May 20, 2004

Related U.S. Application Data

(62) Division of application No. 09/895,753, filed on Jun. 29, 2001, now Pat. No. 6,656,216.

(51) Int. Cl.
*A61F 2/06* (2006.01)

(52) U.S. Cl. .................................................. 623/1.15

(58) Field of Classification Search ............... 623/1.46, 623/1.23, 1.12, 1.13, 1.36, 1.15, 1.42
See application file for complete search history.

(56) References Cited

U.S. PATENT DOCUMENTS

| | | | |
|---|---|---|---|
| 4,733,665 A | 3/1988 | Palmaz | 128/343 |
| 4,800,882 A | 1/1989 | Gianturco | 128/343 |
| 4,886,062 A | 12/1989 | Wiktor | 128/343 |
| 4,931,287 A | 6/1990 | Bae et al. | 424/484 |
| 4,977,901 A | 12/1990 | Ofstead | 128/772 |
| 4,994,560 A | 2/1991 | Kruper, Jr. et al. | 534/10 |
| 5,040,548 A | 8/1991 | Yock | 128/898 |
| 5,059,166 A | 10/1991 | Fischell | 600/3 |
| 5,064,435 A | 11/1991 | Porter | 623/12 |
| 5,087,244 A | 2/1992 | Wolinsky | 604/53 |
| 5,100,429 A | 3/1992 | Sinofsky et al. | 606/195 |
| 5,213,561 A | 5/1993 | Weinstein et al. | 600/7 |
| 5,229,172 A | 7/1993 | Cahalan et al. | 427/536 |
| 5,232,444 A | 8/1993 | Just | 604/96 |
| 5,258,419 A | 11/1993 | Rolando et al. | 522/109 |
| 5,278,200 A | 1/1994 | Coury et al. | 523/112 |
| 5,308,641 A | 5/1994 | Cahalan et al. | 427/2 |
| 5,328,471 A | 7/1994 | Slepian | 604/101 |

(Continued)

FOREIGN PATENT DOCUMENTS

DE 19916086 10/1999

(Continued)

OTHER PUBLICATIONS

U.S. Appl. No. 09/697,106, Hossainy et al.

(Continued)

*Primary Examiner*—(Jackie) Tan-Uyen T. Ho
(74) *Attorney, Agent, or Firm*—Squire, Sanders & Dempsey L.L.P.

(57) ABSTRACT

A composite stent and a method for making the same are provided.

5 Claims, 5 Drawing Sheets

U.S. PATENT DOCUMENTS

| | | | |
|---|---|---|---|
| 5,336,518 A | 8/1994 | Narayanan et al. | 623/1 |
| 5,342,283 A | 8/1994 | Good | 600/8 |
| 5,342,621 A | 8/1994 | Eury | 424/423 |
| 5,344,455 A | 9/1994 | Keogh et al. | 623/11 |
| 5,350,800 A | 9/1994 | Verhoeven et al. | 525/54.2 |
| 5,366,504 A | 11/1994 | Andersen et al. | 623/1 |
| 5,383,928 A * | 1/1995 | Scott et al. | 623/1.12 |
| 5,411,466 A | 5/1995 | Hess | 600/3 |
| 5,415,938 A | 5/1995 | Cahalan et al. | 428/409 |
| 5,429,618 A | 7/1995 | Keogh | 604/266 |
| 5,443,496 A | 8/1995 | Schwartz et al. | 623/1 |
| 5,464,450 A | 11/1995 | Buscemi et al. | 623/6 |
| 5,464,650 A | 11/1995 | Berg et al. | 427/2.3 |
| 5,470,313 A | 11/1995 | Crocker | 604/96 |
| 5,476,509 A | 12/1995 | Keogh et al. | 623/1 |
| 5,500,013 A | 3/1996 | Buscemi et al. | 623/1 |
| 5,551,954 A | 9/1996 | Buscemi et al. | 623/1 |
| 5,554,182 A | 9/1996 | Dinh et al. | 623/1 |
| 5,571,166 A | 11/1996 | Dinh et al. | 623/1 |
| 5,578,073 A | 11/1996 | Haimovich et al. | 623/1 |
| 5,591,224 A | 1/1997 | Schwartz et al. | 623/1 |
| 5,591,227 A | 1/1997 | Dinh et al. | 623/1 |
| 5,599,352 A | 2/1997 | Dinh et al. | 623/1 |
| 5,605,696 A | 2/1997 | Eury et al. | 424/423 |
| 5,624,411 A | 4/1997 | Tuch | 604/265 |
| 5,628,730 A | 5/1997 | Shapland et al. | 604/21 |
| 5,628,785 A | 5/1997 | Schwartz et al. | 623/1 |
| 5,637,113 A | 6/1997 | Tartaglia et al. | 623/1 |
| 5,649,951 A | 7/1997 | Davidson | 606/198 |
| 5,649,977 A | 7/1997 | Campbell | 623/1 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,693,085 A | 12/1997 | Buirge et al. | 623/1 |
| 5,693,376 A | 12/1997 | Fetherston et al. | 427/523 |
| 5,697,967 A | 12/1997 | Dinh et al. | 623/1 |
| 5,700,286 A | 12/1997 | Tartaglia et al. | 623/1 |
| 5,702,818 A | 12/1997 | Cahalan et al. | 428/409 |
| 5,707,385 A | 1/1998 | Williams | 606/192 |
| 5,711,812 A | 1/1998 | Chapek et al. | 118/723 E |
| 5,713,949 A | 2/1998 | Jayaraman | 623/1 |
| 5,716,981 A | 2/1998 | Hunter et al. | 514/449 |
| 5,722,984 A | 3/1998 | Fischell et al. | 606/198 |
| 5,730,698 A | 3/1998 | Fischell et al. | 600/3 |
| 5,766,710 A | 6/1998 | Turnlund et al. | 428/36.1 |
| 5,769,883 A | 6/1998 | Buscemi et al. | 623/1 |
| 5,769,884 A | 6/1998 | Solovay | 623/1 |
| 5,782,742 A | 7/1998 | Crocker | 600/3 |
| 5,800,392 A | 9/1998 | Racchini | 604/96 |
| 5,811,151 A | 9/1998 | Hendriks et al. | 427/2.24 |
| 5,824,048 A | 10/1998 | Tuch | 623/1 |
| 5,824,049 A | 10/1998 | Ragheb et al. | 623/1 |
| 5,826,586 A | 10/1998 | Mishra et al. | 128/898 |
| 5,830,178 A | 11/1998 | Jones et al. | 604/49 |
| 5,837,313 A | 11/1998 | Ding et al. | 427/2.21 |
| 5,840,009 A | 11/1998 | Fischell et al. | 600/3 |
| 5,843,172 A | 12/1998 | Yan | 623/1 |
| 5,851,508 A | 12/1998 | Greff et al. | 424/9.411 |
| 5,857,998 A | 1/1999 | Barry | 604/96 |
| 5,858,556 A | 1/1999 | Eckert et al. | 428/586 |
| 5,858,990 A | 1/1999 | Walsh | 514/44 |
| 5,865,814 A | 2/1999 | Tuch | 604/265 |
| 5,866,113 A | 2/1999 | Hendriks et al. | 424/78.17 |
| 5,871,436 A | 2/1999 | Eury | 600/3 |
| 5,871,437 A | 2/1999 | Alt | 600/3 |
| 5,873,904 A | 2/1999 | Ragheb et al. | 623/1 |
| 5,893,840 A | 4/1999 | Hull et al. | 604/96 |
| 5,897,911 A | 4/1999 | Loeffler | 427/2.25 |
| 5,898,178 A | 4/1999 | Bunker | 250/423 |
| 5,902,631 A | 5/1999 | Wang et al. | 427/2.1 |
| 5,916,234 A | 6/1999 | Lam | 606/198 |
| 5,925,552 A | 7/1999 | Keogh et al. | 435/174 |
| 5,928,916 A | 7/1999 | Keogh | 435/174 |
| 5,951,881 A | 9/1999 | Rogers et al. | 216/41 |
| 5,968,091 A | 10/1999 | Pinchuk et al. | 623/1 |
| 5,968,092 A | 10/1999 | Buscemi et al. | 623/1 |
| 5,971,954 A | 10/1999 | Conway et al. | 604/96 |
| 5,972,027 A | 10/1999 | Johnson | 623/1 |
| 5,972,029 A | 10/1999 | Fuisz | 623/1 |
| 5,980,564 A | 11/1999 | Stinson | 623/1 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,013,099 A | 1/2000 | Dinh et al. | 623/1 |
| 6,015,541 A | 1/2000 | Greff et al. | 424/1.25 |
| 6,019,789 A | 2/2000 | Dinh et al. | 623/1 |
| 6,024,918 A | 2/2000 | Hendriks et al. | 422/44 |
| 6,027,526 A | 2/2000 | Limon et al. | 623/1 |
| 6,033,719 A | 3/2000 | Keogh | 427/2.12 |
| 6,042,606 A | 3/2000 | Frantzen | 623/1 |
| 6,042,875 A | 3/2000 | Ding et al. | 427/2.24 |
| 6,059,752 A | 5/2000 | Segal | 604/107 |
| 6,074,416 A * | 6/2000 | Berg et al. | 623/1.36 |
| 6,080,099 A | 6/2000 | Slater | 600/8 |
| 6,080,190 A | 6/2000 | Schwartz | 623/1 |
| 6,071,305 A | 7/2000 | Brown et al. | 623/1 |
| 6,093,199 A | 7/2000 | Brown et al. | 606/200 |
| 6,096,070 A | 8/2000 | Ragheb et al. | 623/1 |
| 6,099,455 A | 8/2000 | Columbo et al. | 600/3 |
| 6,099,559 A | 8/2000 | Nolting | 623/1.16 |
| 6,099,561 A | 8/2000 | Alt | 623/1.44 |
| 6,106,454 A | 8/2000 | Berg et al. | 600/3 |
| 6,110,483 A | 8/2000 | Whitbourne et al. | 424/423 |
| 6,140,127 A | 10/2000 | Sprague | 435/395 |
| 6,140,431 A | 10/2000 | Kinker et al. | 526/79 |
| 6,149,574 A | 11/2000 | Trauthen et al. | 600/3 |
| 6,153,252 A | 11/2000 | Hossainy et al. | 427/2.3 |
| 6,165,212 A | 12/2000 | Dereume et al. | 623/1.13 |
| 6,168,619 B1 | 1/2001 | Dinh et al. | 623/1.13 |
| 6,203,551 B1 | 3/2001 | Wu | 606/108 |
| 6,214,901 B1 | 4/2001 | Chudzik et al. | 523/113 |
| 6,224,894 B1 | 5/2001 | Jamiolkowski et al. | 424/426 |
| 6,231,590 B1 | 5/2001 | Slaikeu et al. | 606/200 |
| 6,242,041 B1 | 6/2001 | Katoot et al. | 427/2.24 |
| 6,253,443 B1 | 7/2001 | Johnson | 29/557 |
| 6,254,632 B1 | 7/2001 | Wu et al. | 623/1.15 |
| 6,258,121 B1 | 7/2001 | Yang et al. | 623/1.46 |
| 6,262,034 B1 | 7/2001 | Mathiowitz et al. | 514/44 |
| 6,273,850 B1 | 8/2001 | Gambale | 600/3 |
| 6,273,913 B1 | 8/2001 | Wright et al. | 623/1.42 |
| 6,287,628 B1 | 9/2001 | Hossainy et al. | 427/2.3 |
| 6,296,603 B1 | 10/2001 | Turnlund et al. | 600/3 |
| 6,319,520 B1 | 11/2001 | Wuthrich et al. | 424/482 |
| 6,344,035 B1 | 2/2002 | Chudzik et al. | 604/265 |
| 6,355,063 B1 * | 3/2002 | Calcote | 623/1.42 |
| 6,379,379 B1 | 4/2002 | Wang | 623/1.31 |
| 6,379,381 B1 | 4/2002 | Hossainy et al. | 623/1.42 |
| 6,413,272 B1 | 7/2002 | Igaki | 623/1.15 |
| 6,488,701 B1 | 12/2002 | Nolting et al. | 623/1.13 |
| 6,504,307 B1 | 1/2003 | Malik et al. | 315/111.21 |
| 6,524,232 B1 | 2/2003 | Tang et al. | 600/3 |
| 6,554,758 B2 | 4/2003 | Turnlund et al. | 600/3 |
| 6,582,417 B1 | 6/2003 | Ledesma et al. | 604/529 |
| 6,605,114 B1 | 8/2003 | Yan et al. | 623/1.43 |
| 6,645,241 B1 * | 11/2003 | Strecker | 623/1.13 |
| 6,656,216 B1 * | 12/2003 | Hossainy et al. | 623/1.13 |
| 6,861,088 B2 | 3/2005 | Weber et al. | |
| 6,865,810 B2 | 3/2005 | Stinson | |
| 6,869,443 B2 | 3/2005 | Buscemi et al. | |
| 6,878,160 B2 | 4/2005 | Gilligan et al. | |
| 6,887,270 B2 | 5/2005 | Miller et al. | |
| 6,887,485 B2 | 5/2005 | Fitzhugh et al. | |
| 6,890,546 B2 | 5/2005 | Mollison et al. | |

| | | | |
|---|---|---|---|
| 6,899,731 | B2 | 5/2005 | Li et al. |
| 2001/0001806 | A1 | 5/2001 | Turnlund et al. ............ 600/3 |
| 2005/0037052 | A1 | 2/2005 | Udipi et al. |
| 2005/0038134 | A1 | 2/2005 | Loomis et al. |
| 2005/0038497 | A1 | 2/2005 | Neuendorf et al. |
| 2005/0043786 | A1 | 2/2005 | Chu et al. |
| 2005/0049693 | A1 | 3/2005 | Walker |
| 2005/0049694 | A1 | 3/2005 | Neary |
| 2005/0054774 | A1 | 3/2005 | Kangas |
| 2005/0055044 | A1 | 3/2005 | Kangas |
| 2005/0055078 | A1 | 3/2005 | Campbell |
| 2005/0060020 | A1 | 3/2005 | Jenson |
| 2005/0064088 | A1 | 3/2005 | Fredrickson |
| 2005/0065501 | A1 | 3/2005 | Wallace |
| 2005/0065545 | A1 | 3/2005 | Wallace |
| 2005/0065593 | A1 | 3/2005 | Chu et al. |
| 2005/0074406 | A1 | 4/2005 | Couvillon, Jr. et al. |
| 2005/0074545 | A1 | 4/2005 | Thomas |
| 2005/0075714 | A1 | 4/2005 | Cheng et al. |
| 2005/0079274 | A1 | 4/2005 | Palasis et al. |
| 2005/0084515 | A1 | 4/2005 | Udipi et al. |
| 2005/0106210 | A1 | 5/2005 | Ding et al. |
| 2005/0113903 | A1 | 5/2005 | Rosenthal et al. |

FOREIGN PATENT DOCUMENTS

| | | |
|---|---|---|
| EP | 0 627 226 | 12/1994 |
| EP | 0665023 | 8/1995 |
| EP | 0 701 803 | 3/1996 |
| EP | 0 850 604 | 7/1998 |
| EP | 0 972 498 | 1/2000 |
| EP | 0970711 | 1/2000 |
| EP | 0 850 651 | 6/2000 |
| EP | 1 103 234 | 5/2001 |
| WO | WO 90/01969 | 3/1990 |
| WO | WO91/12846 | 9/1991 |
| WO | WO97/45105 | 12/1997 |
| WO | WO 98/23228 | 6/1998 |
| WO | WO99/63981 | 12/1999 |
| WO | WO00/12147 | 3/2000 |
| WO | WO00/64506 | 11/2000 |
| WO | WO01/01890 | 1/2001 |
| WO | WO01/45763 | 6/2001 |
| WO | WO 01/91918 | 12/2001 |
| WO | WO 02/47731 | 6/2002 |

OTHER PUBLICATIONS

U.S. Appl. No. 09/834,012, Hossainy et al.

Barath et al., *Low Dose of Antitumor Agents Prevents Smooth Muscle Cell Proliferation After Endothelial Injury*, JACC 13(2):252A (1989) (Abstract).

Fischell et al., *Low-Dose, β-Particle Emission from 'Stent' Wire Results in Complete, Localized Inhibition of Smooth Muscle Cell Proliferation*, Circulation, vol. 90(6):2956-2963, Dec. 1994.

Hehrlein et al., *Low-Dose Radioactive Endovascular Stents Prevent Smooth Muscle Cell Proliferation and Neointimal Hyperplasia in Rabbits*, Circulation, vol. 92(6):1570-1575, Sep. 15, 1995.

Liermann et al., *Prophylactic Endovascular Radiotherapy to Prevent Intimal Hyperplasia after Stent Implantation in Femoropopliteal Arteries*, CardioVascular and Interventional Radiology 17:12-16, 1994.

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A 15(16):2875-2879 (Nov./Dec. 1997).

Malik et al., *Overview of Plasma Source Ion Implantation Research at University of Wisconsin-Madison*, J. Vac. Sci. Technol. B 12(2):843-849 (Mar./Apr. 1994).

Malik et al., *Sheath Dynamics and Dose Analysis for Planar Targets in Plasma Source Ion Implantation*, Plasma Sources Sci. Technol. 2:81-85 (1993).

Matsumaru et al., *Embolic Materials for Endovascular Treatment of Cerebral Lesions*, J. Biomater. Sci. Polymer Edn. 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6):2490-2498 (1985).

Miyazawa et al., *Effects of Pemirolast and Tranilast on Intimal Thickening After Arterial Injury in the Rat*, J. Cardiovasc. Pharmacol. 30(2):157-162 (1997).

Ohsawa et al., *Preventive Effects of an Antiallergic Drug, Pemirolast Potassium, on Restenosis After Percutaneous Transluminal Coronary Angioplasty*, Am. Heart J. 136(6):1081-1087 (Dec. 1998).

Scheuer et al., *Model of Plasma Source Ion Implantation in Planar, Cylindrical, and Spherical Geometries*, J. Appl. Phys. 67(3):1241-1245 (Feb. 1990).

Serruys et al., *I Like the Candy, I Hate the Wrapper; the $^{32}P$ Radioactive Stent*, Circulation 101:3-7 (Jan. 2000).

Shamim et al., *Measurement of Electron Emission Due to Energetic Ion Bombardment in Plasma Source Ion Implantation*, J. Appl. Phys. 70(9):4756-4759 (Nov. 1991).

Shamim et al., *Measurements of Spatial and Temporal Sheath Evolution for Spherical and Cylindrical Geometries in Plasma Source Ion Implantation*, J. Appl. Phys. 69(5):2904-2908 (Mar. 1991).

Shigeno, *Prevention of Cerebrovascular Spasm by Bosentan, Novel Endothelin Receptor*, Chem. Abstracts 125:212307 (1996).

van der Giessen et al., "Edge Effect" of $^{32}P$ Radioactive Stents is Caused by the Combination of Chronic Stent Injury and Radioactive Dose Falloff, Circ. 104:2236-2241 (Oct. 30, 2001).

Wiesendanger et al., *Contributions Of Scanning Probe Microscopy And Spectroscopy To The Investigation And Fabrication Of Nanometer-Scale Structures*, J. Vac. Sci. Technol. B, 12(2):515-529 (Mar./Apr. 1994).

* cited by examiner

| PREPARE VISCOUS SOLUTION AND PLACE IN CONTAINER HAVING A DRIP NOZZLE | ~401 |

| ROTATABLY POSITION STENT NEAR DRIP NOZZLE | ~402 |

| DRIP VISCOUS SOLUTION ONTO ROTATING STENT | ~403 |

| STOP FLOW OF VISCOUS SOLUTION AND CURE BAND IN SITU | ~404 |

| REPEAT OPERATIONS 401 - 404 IF DESIRED | ~405 |

| STERILIZE STENT AND BAND | ~406 |

| PACKAGE STENT IN STERILE CONTAINER | ~407 |

*FIG. 4*

PREPARE VISCOUS SOLUTION AND PLACE IN CONTAINER HAVING A DRIP NOZZLE ~501

SLIDABLY POSITION STENT NEAR DRIP NOZZLE ~502

DRIP VISCOUS SOLUTION ONTO SLIDING STENT ~503

STOP FLOW OF VISCOUS SOLUTION AND CURE BAND IN SITU ~504

REPEAT OPERATIONS 501 - 504 IF DESIRED ~505

STERILIZE STENT AND BAND ~506

PACKAGE STENT IN STERILE CONTAINER ~507

*FIG. 5*

```
┌─────────────────────────────────────┐
│ PREPARE VISCOUS SOLUTION AND PLACE  │──601
│ IN OPEN CONTAINER                   │
└─────────────────────────────────────┘

┌─────────────────────────────────────┐
│ DIP DISCRETE REGION OF STENT IN THE │──602
│ VISCOUS SOLUTION                    │
└─────────────────────────────────────┘

┌─────────────────────────────────────┐
│ SECURE STENT IN A CENTRIFUGE AND    │──603
│ SPIN THE STENT                      │
└─────────────────────────────────────┘

┌─────────────────────────────────────┐
│ STOP CENTRIFUGE, REMOVE STENT, AND  │──604
│ CURE BAND IN SITU                   │
└─────────────────────────────────────┘

┌─────────────────────────────────────┐
│ REPEAT OPERATIONS 601 - 604 IF      │──605
│ DESIRED                             │
└─────────────────────────────────────┘

┌─────────────────────────────────────┐
│ STERILIZE STENT                     │──606
└─────────────────────────────────────┘

┌─────────────────────────────────────┐
│ PACKAGE STENT IN STERILE CONTAINER  │──607
└─────────────────────────────────────┘
```

FIG. 6

COMPOSITE STENT WITH REGIOSELECTIVE MATERIAL AND A METHOD OF FORMING THE SAME

CROSS REFERENCE

This is a divisional application of U.S. Ser. No. 09/895,753, which was filed on Jun. 29, 2001 now U.S. Pat. No. 6,656,216.

FIELD OF THE INVENTION

The invention relates to intravascular implants. In particular, the present invention relates to stent devices having a regioselective coating. The regioselective coating may contain a therapeutic agent or a radio-opaque material.

BACKGROUND OF THE INVENTION

Characterized by a hardening of the cardiovascular arteries, arteriosclerosis is a medical condition that affects many patients. Fortunately, using medical procedures such as Percutaneous Transluminal Angioplasty (PTA), a sufficient flow of blood can be restored by implanting a tiny mesh tubular structure called a stent inside the affected lumen. In a typical PTA procedure, a stent is crimped about an inflatable balloon attached to the distal end of a catheter, and the catheter is introduced into a patient's vasculature. The catheter's distal end is maneuvered to a site of stenosis, where the balloon is inflated to expand the stent, compress the stenosis, and widen the lumen. The catheter is withdrawn after deflating the balloon.

Normally, the procedure restores a sufficient blood flow, but over time, the flow of blood may again be restricted by vascular problems, such as restenosis, which occur at or near the treatment site.

Restenosis is the renarrowing of a lumen following treatment. A common type of restenosis, known as the "candy wrapper effect", takes its name from stenotic overgrowths appearing at the ends of implanted radioactive stents that remind viewers of a candy wrapper twist-tied about a piece of candy. Typically, the stenotic overgrowths occur within about 2.0 mm of the stent ends. It is believed that the candy wrapper effect is caused in part by balloon expansion, which may injure the lumen, and by a rapid decline in therapeutic radiation levels at the stent ends to a level that no longer prevents or inhibits restenosis. The minimal radiation level proven to prevent or inhibit restenosis is called the threshold level—a radiation dosage below this level being referred to as sub-threshold or sub-therapeutic. The threshold level is estimated to be in the range of approximately 0.5 microcuries and approximately 4.0 microcuries.

Stents may be of various types. Those that are crimped about a balloon and expanded by inflating the balloon are called balloon-expandable stents. Those that are crimped about a balloon and expanded by inflating the balloon with a warm or hot liquid are called thermal self-expanding stents. And, those that are compressed within a tubular sleeve and expanded by withdrawing the tubular sleeve are called self-expanding stents.

Regardless of how deployed, stents may be made of metals, metal alloys, polymers, biodegradable materials, and/or composites thereof. Manufacturing processes such as plasma ion deposition and plasma ion implantation may be used to make stents radioactive and/or radio-opaque. Additionally, stents may be made drug-eluting by forming pores in the material(s) comprising the stent and filling the pores with a drug that performs anti-proliferative, anti-platelet, or anti-clotting functions. For some applications, bioactive materials such as fibronectin, laminin, elastin, collagen, and integregrin may be incorporated into stents. In one process, applying radiation or drugs to stents involves preparing a solution containing the desired therapeutic substance and spraying the solution onto a horizontally positioned, rotating stent via an airbrush that moves laterally back and forth along the length of the rotating stent. In another process, radioactive or drug-eluting stents may be manufactured by affixing hollow or solid biodegradable fibers made of, filled with, or coated with therapeutic agents to the main body of the stent using heat pressing, extrusion molding, solvent heating, and similar attachment methods.

Two problems unsolved by prior approaches to stent design are a drastic tapering of radiation and drug dosage levels at stent ends and difficulty forming elastomeric bands or strips containing desired therapeutic agents in situ about the main body of a stent. Thus, a need exists for a composite stent providing a mechanism for increasing the dosages of drugs and radiation at the stent ends, and for a method providing a procedure for forming elastomeric bands or strips containing desired therapeutic agents in situ about the main body of a stent.

SUMMARY OF THE INVENTION

A composite stent and methods for making the same are provided. In one embodiment a regioselective band is formed in situ on the stent. In one embodiment, the band is made of a regioselective material having a high creep compliance and having a second modulus of elasticity lower than that of a structural material comprising the stent. In one embodiment, the regioselective material is drip-coated or dip-coated on the stent near the ends. In one embodiment, the regioselective material includes a therapeutic agent, which may be a radioactive emitter, an anti-platelet drug, or an anti-proliferative drug.

BRIEF DESCRIPTION OF THE DRAWINGS

FIG. 4 is a flowchart illustrating one embodiment of a method of forming regioselective bands about a stent.

FIG. 5 is a flowchart illustrating one embodiment of a method of forming regioselective strips about a stent.

FIG. 6 is a flowchart illustrating one embodiment of a method of forming a regioselective conformal coating about a stent.

DETAILED DESCRIPTION OF THE INVENTION

Figure 1:
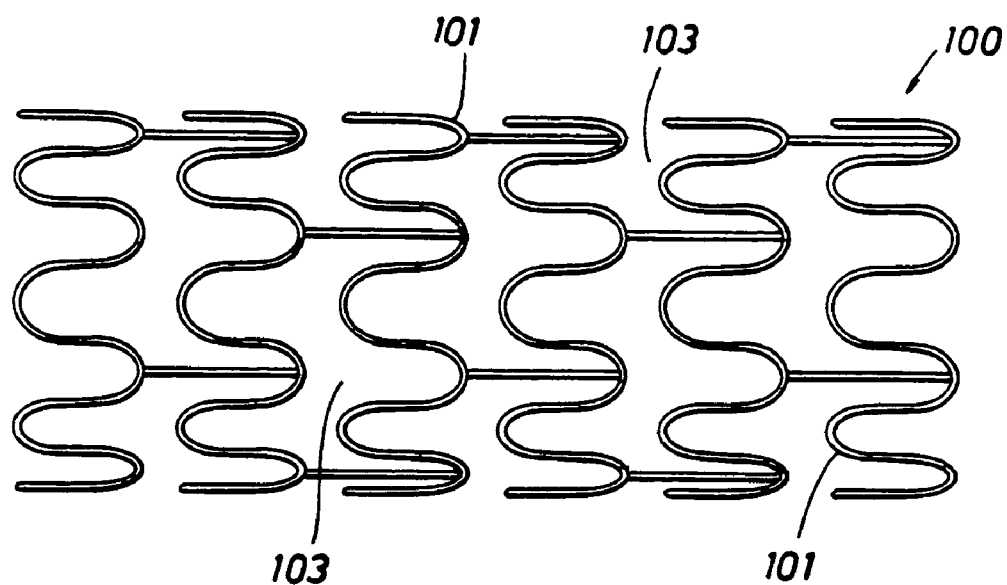
FIG. 1 is an illustration of a stent according to one embodiment of the present invention.

FIG. 1 is an illustration of one embodiment of a stent 100 having an expandable structural frame, which may be formed of metal, polymer, or composite struts or wires. The open spaces found between the struts 101 of the stent 100 are called windows 103. In one embodiment, stent 100 is crimped onto an inflatable balloon attached to the distal end of a catheter, and is expanded by inflating the balloon. Unalloyed metals such as titanium and gold; thermal plastics such as polyester and polycarbonate copolymers; biocompatible metals such as platinum, platinum-iridium alloys, and cobalt-chromium alloys; other metals such as copper alloys; malleable metals such as annealed stainless steels, tungsten, and platinum; and composites of the materials listed above, are examples of materials that may be used to manufacture stent 100. Additional materials may include cobalt-chrome, titanium, and nitinol.

Figure 2:
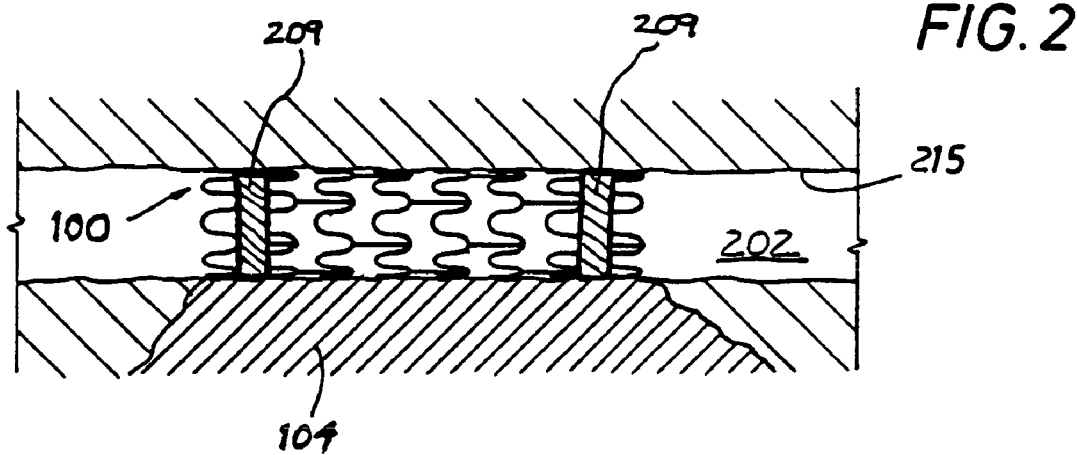
FIG. 2 is an illustration of a stent implanted in a vessel according to one embodiment of the invention.

As shown in FIG. 2, stent 200 may be implanted within a tubular vessel 202 at or near the site 204 of a stenosis to provide mechanical support to the lumen wall 215 of tubular vessel 202. Stent 200 supports an area of the vessel that is in contact with the stent 100. The stent 200 illustratively shown in FIG. 2 includes bands 209 made of a regioselective material that covers only selected discrete regions of the stent. In other embodiments, the regioselective material may be applied to stent 200 as strips, as a conformal coating, or as a compression-fitted sleeve. Use of regioselective bands 209 offers an improvement over the prior art in that it allows simultaneous delivery of radiation and drug dosimetries. Additionally, use of bands 209 permits the tailoring of radiation and/or drug dosimetries within a desired range at discrete areas of the stent, such as near the stent ends, where restenosis is prone to occur. For example, an aspect of the present invention provides regioselective bands 209 having a therapeutic agent incorporated therein that are positioned near the ends of stent 200 to increase the therapeutic dosimetry near the stent ends in an effort to prevent or inhibit restenosis.

In one embodiment, the regioselective material forming bands 209 is applied to the stent 200 while the stent 200 is a compressed position. Because the stent 200 may later be expanded at a treatment site, it is important to choose a regioselective material that will expand as stent 200 expands without tearing and without exerting a harmful compressive restoring force. One way of ensuring proper stent expansion is to use a regioselective material having a high creep compliance and a modulus of elasticity lower than that of the structural material forming the main body of stent 200.

Related quantative measurements of a material's reaction to stress and strain, creep compliance and modulus of elasticity vary for each particular type of material. For example, creep compliance is the ratio of strain to the applied stress, while the modulus of elasticity is the ratio of the applied stress to strain. Most materials used in the manufacture of stents are viscoelastic materials, which are materials formed of a combination of viscous and elastic components. Materials having a low creep compliance, such as purely elastic materials, tend to exert an immediate and strong restoring force when stretched or compressed. On the other hand, materials having a high creep compliance, such as purely viscous materials, tend to exert a gradual and weak restoring force when compressed or stretched.

In one embodiment, the material or materials used to form regioselective bands 209 or strips (not shown) are viscoelastic materials having a high creep compliance because such materials are easily expandable and typically exert a gradual and weak restoring force that avoids collapsing or substantially deforming an expanded stent over time. In one embodiment, the creep compliance may be approximately 0.3846 Giga-Pascals $(GPa)^{-1}$ and may range from approximately 0.5 $GPa^{-1}$ to approximately 10.0 $GPa^{-1}$. In another embodiment, elastic materials may be used provided care is taken to ensure that the stent in its expanded state is capable of sustaining the elastic material's immediate and strong restoring force without collapsing or substantially deforming the expanded stent over time.

Anti-proliferative drugs, anti-platelet drugs, TB3A inhibitors, and nictric oxide donors, bioactive drugs, blood compatible matrices, and radioactive emitters may be incorporated in the structural and/or regioselective materials forming stent 200. In one embodiment, the blood compatible matrices and bioactive drugs may be bio-absorbable. Substances that may be incorporated in a stent or its components to make the stent visible under a fluoroscope include heavy rare earth metals such as gold, micronized tantalum, platinum-iridium, and similar materials. Examples of blood compatible matrices and bioactive drugs that may be used to form a regioselective band 209 or a regioselective strip illustratively include:

a. DURAFLO® or other coatable Heparin Derivative (In this case, the drug itself can form the regioselective material);
   b. Phosphoryl choline;
   c. Ethylene vinyl alcohol (EVAL);
   d. Polyanhydrides;
   e. Polyesters;
   f. Polyphosphazenes;
   g. Polyhydroxybutyrate;
   h. Valerate (PHB, PHV) (these materials belong to an absorbable family);
   i. Polyurethanes such as Biospan®, Biospan-S®, Biospan P®, and Elastion;
   j. Polyvinylidene fluoride (PVDF);
   k. Poly (butyl methacrylate) (PBMA);
   l. Kraton™;
   m. Hexafluoropropylene (PDF-6-HEFP);
   n. Hyaluronic Acid;
   o. Water Soluble chondroitin sulfate;
   p. Poly (ethylene glycol) (PEG), Poly (Vinyl Pyrrolidine) (PVP);
   q. PCL-CO-PEG, PLA-CO-PEG; polybutylene tarephthalate (Polyactive) (these materials belong to an absorbable blood compatible family); and
   r. Poly alpha-hydroxy acids (PLA, PCL, PGA, etc.).

It is noted that the above list is not exhaustive, and that additional materials well known to persons skilled in the art may be used. Materials a, b, n, o, p, q above are examples of polymer materials that may be used to form polymeric bands. Materials n-r above are examples of bio-absorbable matrices. In one embodiment, in situ tissue components may be used to facilitate better tissue compatibility. In some cases, use of such tissue components may promote possible secondary endothelialization (EC) in-growth into the stent. In one embodiment, the entire length of the stent may be created with the EC-conductive materials, and the stent ends may be further coated with radioactivity. In another embodiment, non-coagulant, co-components like DURAFLO ®, or low molecular weight heparin (LMWH), may be used to prevent any acute thrombogenic episodes, and to address the three issues commonly associated with radioactive struts; namely, late healing, candy wrapper effect, and late thrombosis.

Figure 3:
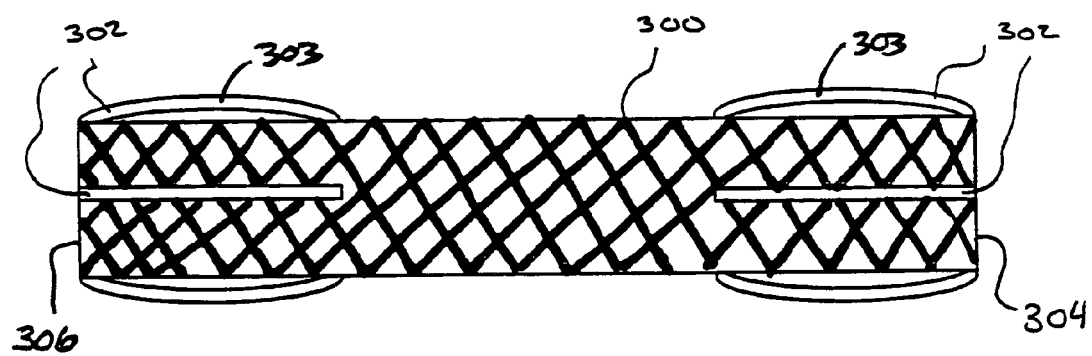
FIG. 3 is an illustration of a stent according to another embodiment of the present invention.

FIG. 3 is an illustration of a stent according to another embodiment of the invention in which a plurality of strips 302 are spaced circumferentially around the stent 300. As described above with respect to bands 209, strips 302 may be formed of a regioselective material having a high creep compliance and a modulus of elasticity lower than that of the structural material forming the main body of stent 300. In one embodiment, a therapeutic agent is incorporated in the regioselective material forming strips 302. Though shown in FIG. 3 as being coupled with stent 300 near its ends (304, 306), strips 302 may be mounted at any location, circumferentially, diagonally, horizontally, and/or longitudinally, on stent 300.

In one embodiment, regioselective bands 209 or regioselective strips 302 may be preformed and then affixed to a stent using a biocompatible medical adhesive. Fibrin glue, cyanoacrylate, Focal Seal®, carboxymethyl cellulose, gelatin- resourcinresorcin-formaldehyde glue (GRF), silk elastin, tropoelastin added with an in situ cross-linker such as lysine peroxidase and similar materials, water soluble chondroitin sulfate, are examples of biocompatible adhesives that may be used.

FIGS. 4 and 5 are flowcharts illustrating embodiments of a drip coating process according to one embodiment of the invention, wherein a viscous solution containing a desired regioselective material and a therapeutic agent is dripped onto a rotating or horizontally moving stent, to form regioselective bands 209 or regioselective strips 302 on the main body of a stent. In FIG. 4, the process begins at Block 401 by preparing a viscous solution of PCL and/or polyethylene glycol (PEG) which contains a dissolved or suspended therapeutic agent, placing the solution in a container having a drip nozzle. In one embodiment, the drug or polymer comprising the solution is approximately 15% by weight of a solvent such as dimethylsulfoxide (DMSO). At block 402, a stent rotatably affixed to a mandrel in a relaxed, unstretched condition is positioned near the mouth of the drip nozzle, which may be disengageably fixed at a discrete section of the stent. In one embodiment, a motor may be attached to the mandrel to rotate the stent about its longitudinal axis in a substantially horizontal plane.

At Block 403, the solution is dripped onto the rotating stent such that a semi-solid or solid conformal band results after one or more complete revolutions of the stent. In one embodiment, the viscosity of the solution is such that the solution streams from the drip nozzle like a liquid fiber and loops about the stent to form a concentric annular band having a substantially tubular diameter of approximately 0.5 to approximately 5.0 microns. In another embodiment, the viscosity of the solution is such that the solution streams from the drip nozzle like a liquid fiber and spreads somewhat laterally across a discrete portion of the stent to form a conformal band of substantially uniform width of approximately 0.5 mm to about 3.0 mm, and a variable elastic or semi-elastic thickness of approximately 1.0 to approximately 5.0 microns when cured. At Block 404, the flow of viscous solution is stopped, and the band is cured by either washing away the solvent, or by air-drying the band. At block 405, the process may be repeated at the same or another discrete area of the stent until a desired dosimetry profile and/or regioselective thickness is achieved. At Block 406, the stent may be sterilized with radiation, heat, or chemicals. Because individual therapeutic agents degrade at different temperatures and react differently when brought into contact with radiation or chemicals, care should be taken to ensure that the sterilization method used does not adversely affect the therapeutic agent incorporated in the regioselective material. In one embodiment, an electron beam sterilization method is used in which the stent is subjected to a 3.5 Mrad. At Block 407, the stent may be packaged in a sterile container for delivery to a user.

In FIG. 5, the process begins at Block 501 by preparing a viscous solution of PCL and/or polyethylene glycol (PEG) which contains a dissolved or suspended therapeutic agent, placing the solution in a container having a drip nozzle. In one embodiment, the drug or polymer comprising the solution is approximately 15% by weight of a solvent such as dimethylsulfoxide (DMSO). At block 502, a stent slidably affixed to a mandrel in a relaxed, unstretched condition is positioned near the mouth of the drip nozzle, which is fixed in a static position. In an alternative embodiment, the stent may be fixed in a static position, and the mandrel moved slidably along the length of the stent. In one embodiment, a motor may be attached to the mandrel to slidably move the stent beneath the drip nozzle. In another embodiment, the motor may rotate the stent as it slides the stent horizontally near the drip nozzle.

At Block 503, the solution may be dripped onto the sliding stent such that a semi-solid or solid conformal strip results after one or more complete passes of the stent. In one embodiment, the viscosity of the solution is such that the solution streams from the drip nozzle like a liquid fiber and lays along the stent to form a longitudinal strip having a substantially tubular diameter of approximately 0.5 to approximately 5.0 microns. In another embodiment, the viscosity of the solution is such that the solution streams from the drip nozzle like a liquid fiber and spreads somewhat laterally across a discrete portion of the stent to form a conformal strip having a substantially uniform width of approximately 0.5 mm to about 3.0 mm, and a variable elastic or semi-elastic thickness of approximately 1.0 to approximately 5.0 microns when cured. At Block 504, the flow of viscous solution is stopped, and the strip is cured by either washing away the solvent, or by air-drying the strip. At block 505, the process may be repeated at the same or another discrete area of the stent until a desired dosimetry profile and/or regioselective thickness is achieved. At Block 506, the stent may be sterilized with radiation, heat, or chemicals. Because individual therapeutic agents degrade at different temperatures and react differently when brought into contact with radiation or chemicals, care should be taken to ensure that the sterilization method used does not adversely affect the therapeutic agent incorporated in the regioselective material. In one embodiment, an electron beam sterilization method is used in which the stent is subjected to approximately 3.5 MRad. At Block 507, the stent may be packaged in a sterile container for delivery to a user.

With reference to the methods described above, the distance separating the outer surface of the stent from the tip of the drip nozzle may vary depending on the viscosity of the solution, the air temperature, and the air humidity. For example, very dry hot air may necessitate placing the stent close to the drip nozzle to prevent the viscous solution from drying too quickly. Alternatively, if the air is cool and humid, the stent may be placed further away from the drip nozzle. Similarly, using a very viscous solution may necessitate placing the stent close to the drip nozzle to avoid unnecessarily stretching the solution via free fall. Alternatively, using a less viscous solution may allow the stent to be placed further away from the drip nozzle. In one embodiment, a viscosity of approximately 100 centipoises (cP) at room temperature is used with a distance of approximately 5.0 cm separating the stent from the drip nozzle. Illustratively, the viscosity may range from approximately 5.0 cP to 1,000 cP at room temperature, and the distance may range from approximately 1.0 cm to approximately 15.0 cm. In another embodiment, a viscosity of approximately 50.0 cP to approximately 500 cP at room temperature is used, with a distance of approximately 3.0 cm to approximately 8.0 cm separating the stent from the drip nozzle.

In one embodiment, air-drying the band or strip involves rotating the stent in a stream of air, which temperature is in the range of approximately room temperature to approximately 70° C., for approximately 5.0 seconds to approximately 1.50 minutes. Because different drugs degrade at different temperatures, it should be noted that the temperature involved in the curing process may vary depending on the type of drug used. Accordingly, the air temperature should be monitored to ensure that it remains within acceptable limits. Similarly, the length of time required to cure the band varies depending on the viscosity of the material(s) comprising the band. For example, the more viscous a material, the longer the time needed to cure it thoroughly.

The rotation speed of the motor, the viscosity of the composition, and the flow rate of the drip nozzle may be adjusted as desired to modify the band or strip layers. Generally, with the above mixes, the best results for bands are obtained using rotational speeds in the range of approximately 1.0 rpm to approximately 60.0 rpm, with a drip nozzle flow rate appropriately adjusted to yield a smooth, conformal coating. The flow rate may be varied depending on the speed at which the stent is rotated. For example, a slow rotation may necessitate a slow drip nozzle flow rate, and vice versa. In one embodiment, a flow rate of approximately 0.1 ml/min is used, with the flow rate variable in the range of approximately 0.01 ml/min to approximately 2.0 ml/min. While the above methods were illustratively described with reference to a single stent, it should be noted that the methods may be used to process multiple stents simultaneously. For example, two or more stents may be coupled to a frame, positioned near a corresponding number of drip nozzles, and then rotated or slided, cured, and sterilized.

FIG. 6 illustrates one embodiment of an alternate method of uniformly and integrally coating a discrete area of a stent with a regioselective material containing a therapeutic agent. In one embodiment, the discrete area of the stent is a band ranging from approximately 0.5 microns wide up to and including the entire length of the stent. The method begins at Block 601 by preparing a solution of PCL and/or poly ethylene glycol (PEG) containing a dissolved or suspended thrombotic agent as described above, and placing the solution in an open container. The viscosity of the solution is chosen such that the coating will uniformly and integrally spread along the surface area of the stent when the stent is spun in a centrifuge. At Block 602, a portion of the stent to be coated is dipped into the viscous solution and removed. Alternatively, a discrete portion of the stent may be coated with the solution using a spraying or brushing method. At Block 603, the stent is secured in a centrifuge and spun to spread the solution uniformly and integrally along a portion of the stent. At Block 604, the stent is removed from the centrifuge and cured either by allowing it to air-dry, or by coating it with a solvent, such as methanol. At block 605, the process may be repeated at the same or another discrete area of the stent until a desired dosimetry profile and/or regioselective thickness is achieved. At Block 606, the stent may be sterilized with radiation, heat, or chemicals. Because individual therapeutic agents degrade at different temperatures and react differently when brought into contact with radiation or chemicals, care should be taken to ensure that the sterilization method used does not adversely affect the therapeutic agent incorporated in the regioselective material. In one embodiment, an electron beam sterilization method is used in which the stent is subjected to approximately 3.5 MRad. At Block 607, the stent may be packaged in a sterile container for delivery to a user. While the above method was illustratively described with reference to a single stent, it should be noted that the method may be used to process multiple stents simultaneously, as previously described.

With reference to the centrifugation method described above, a viscosity of approximately 100 cP at room temperature is used, with a rotational speed of approximately 7,000 rev/min for approximately 1.0 min. Illustratively, the viscosity may range from approximately 100 cP to approximately 1,000 cP at room temperature with rotational speeds in the range of approximately 2,000 rev/min to approximately 10,000 rev/min and times of approximately 20.0 seconds to approximately 2.0 min. The rotational speed of the centrifuge, the viscosity of the composition, the air temperature and humidity inside the centrifuge, and time of rotation may be adjusted as desired to modify the band layers. For example, a very viscous material may require higher rotational speeds and longer drying times than a low viscous material.

An advantage provided by the centrifugation process over the prior art is that the process produces a thin conformal coating relatively free from defects such as blobs, rips, and tears.

Although the invention has been described with reference to preferred embodiments, persons skilled in the art will recognize that changes may be made in form and in detail without departing from the spirit and scope of the invention.

What is claimed is:

1. A stent, comprising:
    a body having a first end and a second end and a middle segment between the first and second ends; and
    a plurality of polymeric strips circumferentially spaced from each other around the body of the stent, wherein the plurality of polymeric strips are disposed at or adjacent to the first and/or second end of the stent and do not extend into the middle segment of the body, wherein the plurality of strips have a modulus of elasticity lower than the body of the stent, and wherein the plurality of polymeric strips are in contact with the body of the stent.

2. The stent of claim 1, wherein the plurality of polymeric strips include a drug.

3. The stent of claim 1, wherein the plurality of polymeric strips include a bioabsorbable material.

4. The stent of claim 3, wherein the bioabsorbable material is selected from the group consisting of hyaluronic acid, water soluble chondroitin sulfate, poly(ethylene glycol), poly(vinyl pyrrolidine), poly(caprolactone-co-ethylene glycol), poly(lactic acid-co-ethylene glycol), polybutylene terephthalate and poly alpha-hydroxy acids.

5. The stent of claim 2, wherein the drug is selected from the group consisting of anti-proliferative drugs, anti-platelet drugs, TB3A inhibitors and nitric oxide donors.

* * * * *

UNITED STATES PATENT AND TRADEMARK OFFICE
Certificate

Patent No. 7,169,173 B2

Patented: January 30, 2007

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Syed F. A. Hossainy, Fremont, CA (US); Orlando Padilla, Laguna Beach, CA (US); Daryush Mirzaee, Sunnyvale, CA (US); and Fuh-Wei Tang, Temecula, CA (US).

Signed and Sealed this Sixth Day of March 2012.

S. THOMAS HUGHES
*Supervisory Patent Examiner*
Art Unit 3731
Technology Center 3700